United States Patent
Richards et al.

(10) Patent No.: US 8,215,301 B2
(45) Date of Patent: *Jul. 10, 2012

(54) NOSE CANNULA HEATED/HUMIDIFIED GAS DELIVERY SYSTEM

(75) Inventors: Fredrick M. Richards, Plymouth, MA (US); Gregory S. King, Cazenovia, NY (US); Kevin Thomas Farrell, Marshfield, MA (US)

(73) Assignee: Smiths Medical ASD, Inc., Keene, NH (US)

( * ) Notice: Subject to any disclaimer, the term of this patent is extended or adjusted under 35 U.S.C. 154(b) by 803 days.

This patent is subject to a terminal disclaimer.

(21) Appl. No.: 12/145,760

(22) Filed: Jun. 25, 2008

(65) Prior Publication Data

US 2009/0056711 A1    Mar. 5, 2009

Related U.S. Application Data

(63) Continuation-in-part of application No. 11/846,765, filed on Aug. 29, 2007.

(51) Int. Cl.
*A61M 16/00* (2006.01)
(52) U.S. Cl. ......... 128/204.17; 128/204.18; 128/204.21; 128/205.23; 128/207.18
(58) Field of Classification Search .............. 128/204.17, 128/204.18, 204.21, 204.22, 204.23, 205.12, 128/206.22, 207.18
See application file for complete search history.

(56) References Cited

U.S. PATENT DOCUMENTS

| | | | | | |
|---|---|---|---|---|---|
| 5,069,222 | A | * | 12/1991 | McDonald, Jr. | 600/537 |
| 5,137,017 | A | * | 8/1992 | Salter | 128/207.18 |
| 5,558,084 | A | * | 9/1996 | Daniell et al. | 128/203.17 |
| 6,167,883 | B1 | * | 1/2001 | Beran et al. | 128/203.17 |
| 2002/0122746 | A1 | * | 9/2002 | Yamamori et al. | 422/83 |
| 2003/0189492 | A1 | * | 10/2003 | Harvie | 340/573.1 |
| 2004/0015092 | A1 | * | 1/2004 | Pettersson | 600/532 |
| 2004/0230108 | A1 | * | 11/2004 | Melker et al. | 600/340 |
| 2007/0107737 | A1 | * | 5/2007 | Landis et al. | 128/207.18 |
| 2007/0113856 | A1 | * | 5/2007 | Acker et al. | 128/207.14 |
| 2007/0283957 | A1 | * | 12/2007 | Schobel et al. | 128/204.17 |
| 2008/0028850 | A1 | * | 2/2008 | Payton et al. | 73/204.19 |

FOREIGN PATENT DOCUMENTS

| | | | |
|---|---|---|---|
| DE | 3709122 A1 | * | 9/1988 |
| EP | 1481702 | | 12/2004 |
| EP | 1715909 | | 11/2006 |
| WO | WO 2005011556 | | 2/2005 |
| WO | WO 2006019323 A1 | * | 2/2006 |
| WO | WO 2006072231 A2 | * | 7/2006 |

OTHER PUBLICATIONS

Machine Translation of DE3709122A1, Lang et al., Sep. 29, 1988, Non-sterile temp. sensor for artificial breathing hose inserted in a protective sleeve, all pages.*

* cited by examiner

*Primary Examiner* — Clinton T Ostrup
(74) *Attorney, Agent, or Firm* — Luedeka Neely Group, P.C.

(57) ABSTRACT

A low flow heated/humidified respiratory gas delivery system, especially useful for low flow rates as preferred in the treatment of neonate and other such patients, wherein the respiratory gas is heated and humidified as desired for delivery to the patient and the temperature is monitored at the point of delivery to the patient.

7 Claims, 3 Drawing Sheets

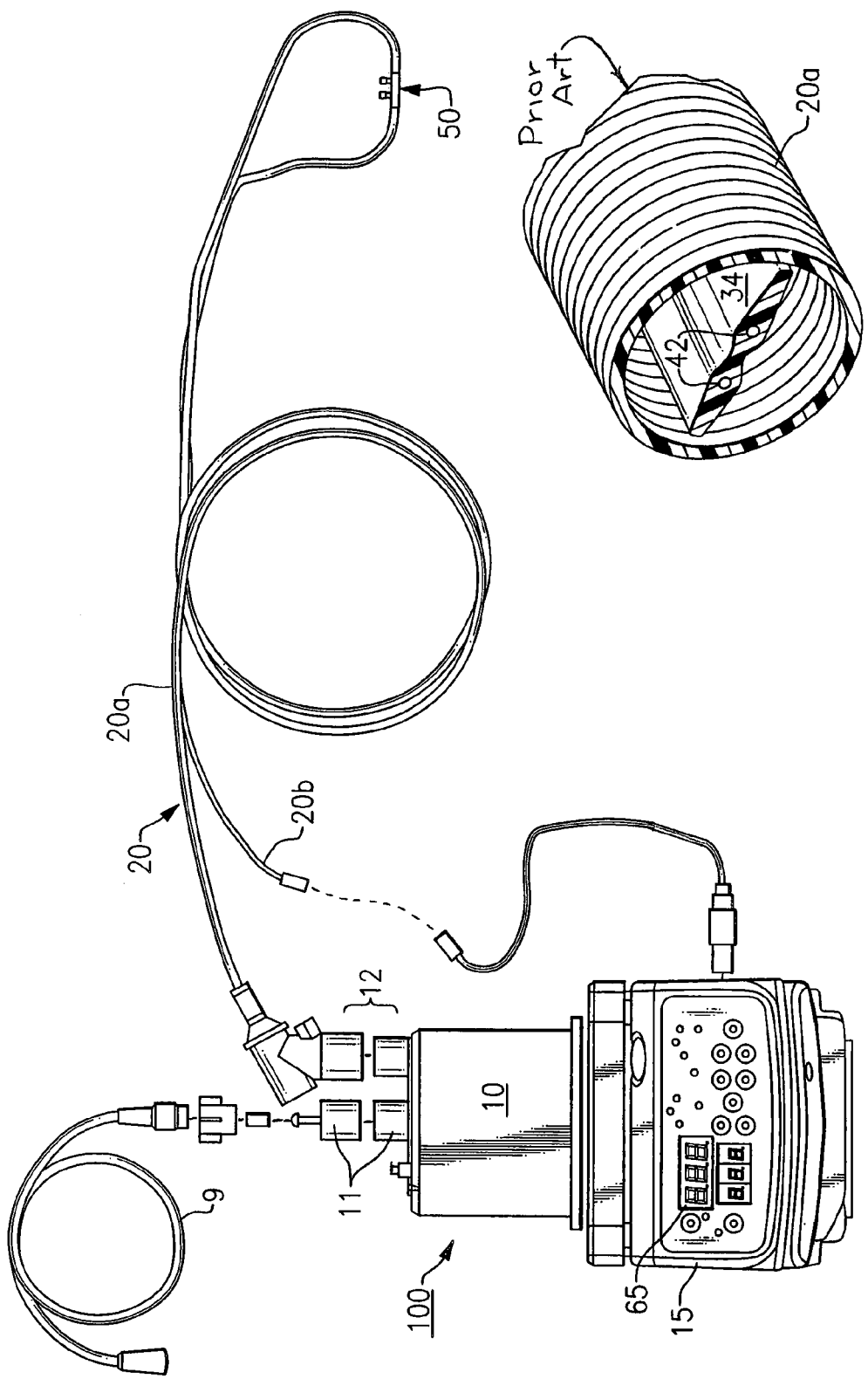

US 8,215,301 B2

NOSE CANNULA HEATED/HUMIDIFIED GAS DELIVERY SYSTEM

CROSS REFERENCE TO RELATED APPLICATION

This application is a continuation-in-part of U.S. application Ser. No. 11/846,765 filed Aug. 29, 2007 entitled NOSE CANNULA HEATED/HUMIDIFIED GAS DELIVERY SYSTEM.

FIELD OF THE INVENTION AND BACKGROUND

This invention relates in general to respiratory care and therapy, and, in particular, to the controlled delivery of heated and/or humidified respiratory gases to a user being so cared for or treated. More particularly, this invention relates to controlling the temperature of the gas or gases used for such care or treatment at the point of the delivery of such gas or gases to the user.

In the administration of heated and/or humidified gas or gases to a user or patient, especially those considered as requiring neonatal care, such as premature infants and some pediatric patients, it is desirable to closely control and monitor the temperature at which the gas or gases are delivered. Such gases may be oxygen, heliox, nitrogen, or combinations thereof, as well as other gases known to those healthcare providers or clinicians providing such services. For convenience of illustration the term "gas" will be used hereinafter, but it is to be understood that such term includes a single gas as well as a combination of gases used in respiratory care and therapy by a user or patient. Also, for purposes of convenience, the term user or patient will be referred to hereinafter as "patient".

Respiratory gas delivered to, for example, neonate patients is preferably delivered at a low flow rate, between about 1 and about 15 liters per minute. When heated gas flows through a delivery conduit at such low flow rates, the temperature of the gas will decrease in transit to the patient delivery point, resulting in a lower temperature gas being applied to the patient and condensate being formed in the gas delivery conduit. The lower temperature gas can cause irritation of the nares and other discomforts to the patient, as well as reducing the core temperature of the patient. In addition, the accumulation of condensate can result in the gas propelling a bolus of condensate into the patient's respiratory system causing coughing or choking. Accordingly, it is highly desirable that the temperature of the respiratory gas being delivered to the patient be controlled at the very point where the gas is being delivered to the patient, to insure that the desired gas temperature is being applied to the patient with the desired humidification level. Such controlled delivery will increase the patient's comfort level, and reduce the amount of condensate heretofore occurring in available heated-gas delivery systems.

SUMMARY

The above and other needs are met by a low flow heated/humidified respiratory gas delivery system, especially useful for low flow rates as preferred in the treatment of neonate and other such patients, wherein the respiratory gas is heated and humidified as desired for delivery to the patient and the temperature is monitored at the point of delivery to the patient. In this manner, the gas temperature can be controlled so that the temperature of the gas being applied to the patient is accurately maintained, and the formation of condensate in the delivery conduit is minimized to reduce accumulation. Patients are believed to be much more tolerable of such a treatment, and less likely to be disengaged therefrom. Fewer adverse reactions, such as abrasions, are believed to be incurred, and the patient can still be fed or can eat without necessitating the removal or disconnecting of the gas delivery system.

BRIEF DESCRIPTION OF THE DRAWINGS

Further advantages of the invention are apparent by reference to the detailed description when considered in conjunction with the drawing figures, which are not to scale so as to more clearly show the details, wherein like reference numbers indicate like elements throughout the several views, and wherein:

FIG. 1 is an illustration of the delivery system wherein a delivery tube or conduit is coupled with a suitable heater to deliver heated/humidified gas to a patient through a nose cannula;

FIG. 2 is an enlarged partial sectional view of a portion of the delivery tube or conduit through which heated/humidified gas is delivered to the nose cannula to illustrate the manner in which the respiratory gas is heated;

DETAILED DESCRIPTION

Figure 3:
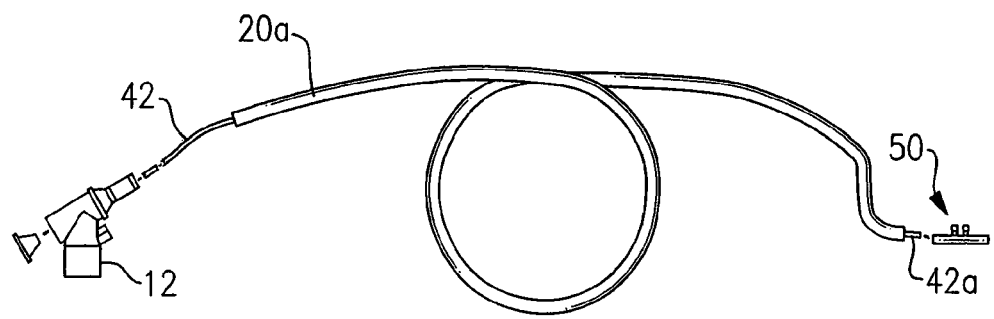
FIG. 3 is an exploded illustration of a portion of the delivery tube or conduit through which heated/humidified gas is delivered to the nose cannula for application to the patient.

Referring now to FIG. 1, there is illustrated a respiratory gas delivery system 100 wherein a source of suitable respiratory gas (not shown) is coupled to a connector 8 and passes through a conduit 9 for connection to a humidification chamber which may be, for example, a reusable or a single-patient-use humidification or nebulizing chamber 10 through an inlet coupling 11. As is known to those skilled in the art, the respiratory gas may nebulize a liquid, or a liquid with medicant, contained in the chamber 10, or the respiratory gas may be bubbled through the liquid if desired, and the heated gas passed from the chamber 10 with, or without, a vapor mist as prescribed by a healthcare provider or clinician. The temperature of the respiratory gas passing from the chamber 10 is heated by means of a heater 15, such as the heater disclosed in U.S. Pat. No. 6,988,497 assigned to Smiths Medical ASD, Inc. of Rockland, Mass.

The heated gas is passed out from the chamber 10 through an outlet connector 12 and passes through a standard flexible delivery tube or conduit 20, for delivery to a patient through a nose cannula 50. As illustrated in FIG. 2, the delivery tube or conduit 20 may be of the type disclosed in Anthony V. Beran, et al, U.S. Pat. No. 6,167,883, "MEDICAL AIR-HOSE INTERNAL FLOW HEATER" assigned to the assignee of the present invention and the disclosure of which is incorporated herein by reference. As illustrated therein, a flexible ribbon 34 spans the width of a first portion 20a of the flexible tube 20, and carries therein a heating element 42, preferably an electrically conductive wire or plurality of wires connected to a power supply in order to heat the flow of gas traveling within this portion of the delivery tube 20a. While there is illustrated a heater wire 42 carried within the tube 20 by a flexible ribbon 34, the wire 42 may be positioned within the tube 20 without being supported by a flexible ribbon such as, for example, by being coiled along the interior of the tube 20.

Figure 4:
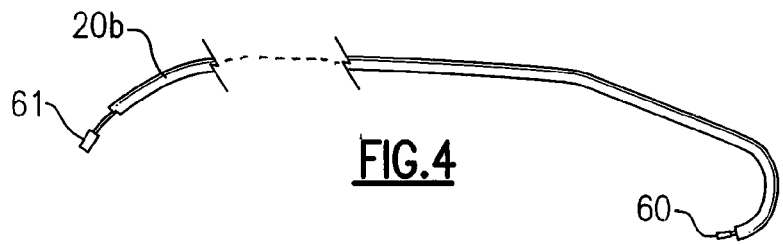
FIG. 4 is an exploded illustration of another portion of the delivery tube or conduit through which the temperature of the heated/humidified gas is monitored at the point of delivery to the patient.

As better illustrated in FIG. 4, the distal portion 42a of the heating element 42 terminates at the entrance into the nose cannula 50, at the point at which the heated gas is applied or administered essentially directly to the patient. In this manner, the respiratory gas is heated all the way through the first portion 20a of the flexible tube 20 so that the slow rate of flow of the respiratory gas will not cool the gas below the desired temperature, but is applied directly to the patient at the clinician prescribed temperature level. Maintaining the respiratory gas heated to the prescribed temperature level at the point of delivery to the patient, will thereby minimize the occurrence of condensate formation.

Figure 5:
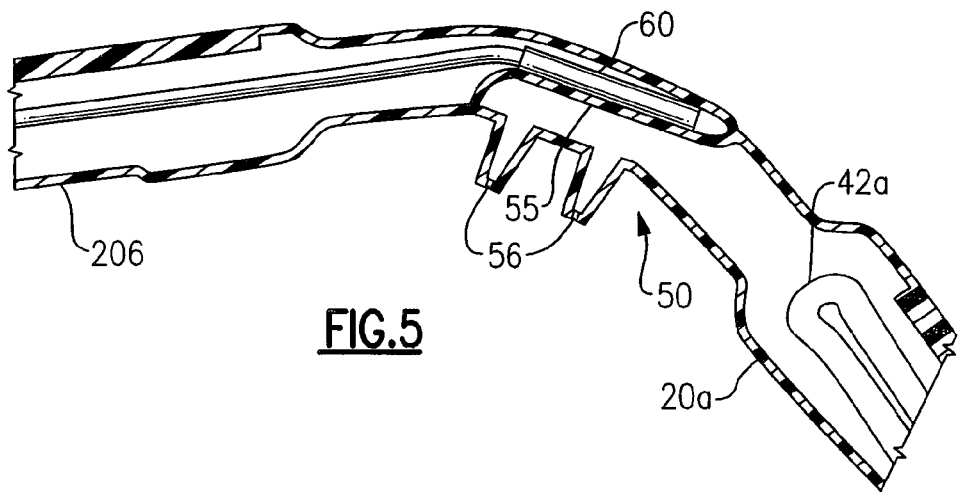
FIG. 5 is an enlarged illustration of a portion of the delivery tube or conduit illustrated in FIGS. 3 and 4 in an embodiment in which the nose cannula is formed with a partition which separates the input of respiratory gas to the patient from the sensing of the gas temperature for controlling the operation of the heater to better illustrate the monitoring of the temperature of the gas as it is being applied to the patient, and the path of the air flow.
Figure 6:
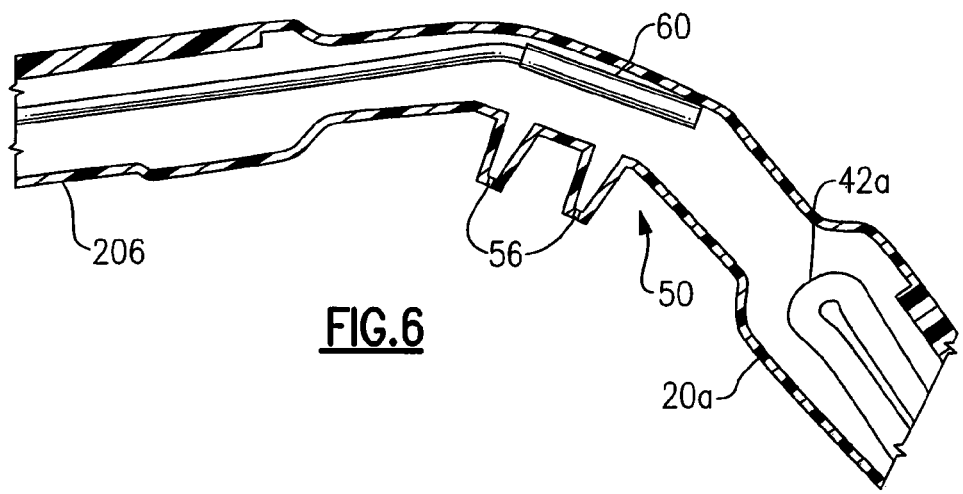
FIG. 6 is an enlarged illustration of a portion of the delivery tube or conduit illustrated in FIGS. 3 and 4 in an embodiment in which the nose cannula is formed without a partition which separates the input of respiratory gas to the patient from the sensing of the gas temperature for controlling the operation of the heater to better illustrate the monitoring of the temperature of the gas as it is being applied to the patient, and the path of the air flow.
Figure 7:
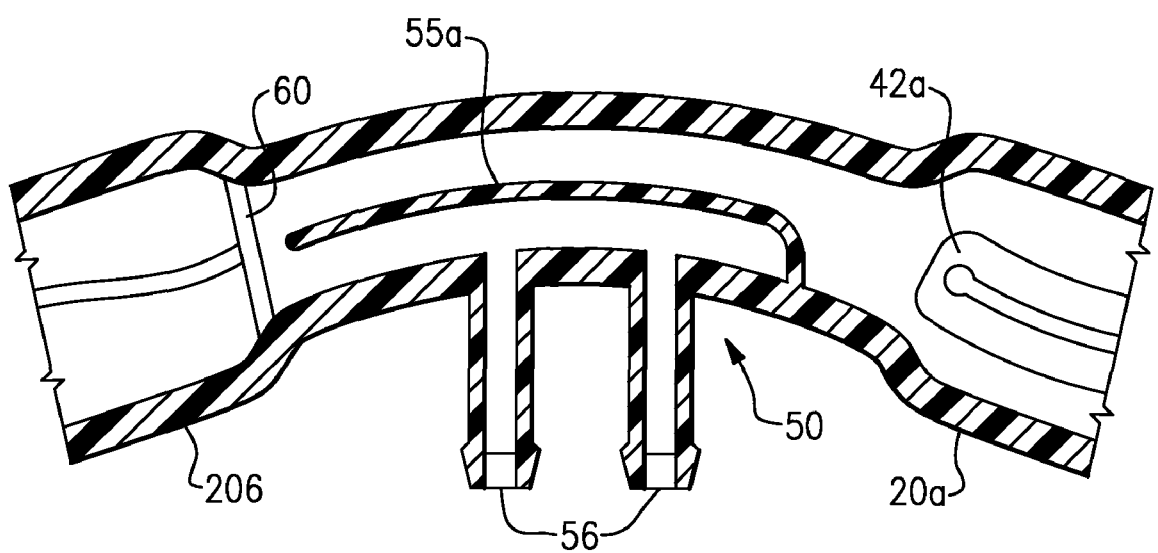
FIG. 7 is an enlarged illustration of a portion of the delivery tube or conduit illustrated in FIGS. 3 and 4 in an embodiment in which the nose cannula is formed with a partition which directs the input of respiratory gas in a flow path in direct fluid communication with the gas temperature sensor immediately prior to the gas being applied to the patient for controlling the operation of the heater to better illustrate the monitoring of the gas temperature and the path of the respiratory gas flow.

The temperature of the respiratory gas being delivered to the nose cannula 50 through the flexible tube 20, is controlled by a sensor 60, preferably a thermister, which is carried within a second portion 20b of the flexible tube 20 extending from an input 13 from the heater 15 to a position within the nose cannula 50 directly adjacent to the point at which the respiratory gas is applied or administered, 56, essentially directly to the patient, as best illustrated in FIGS. 5-7. The positioning of the sensor in this position, in the nose cannula, will give direct feedback to the clinician of the temperature of the respiratory gas entering the patient's nose. The output from the sensor 60 may, if desired, be coupled to a digital display 65 to provide the clinician with an accurate visual display of the temperature of the respiratory gas as actually being administered to the patient.

Because the air flow is constantly flowing from the outlet 12 of the chamber 10 to the patient's nose cannula 50, only inspiratory air is delivered to the patient through the first portion 20a of the flexible tube 20. Accordingly, re-breathing of exhaled air by the patient is substantially minimized or eliminated entirely.

As best illustrated in the embodiment of FIG. 5, the nose cannula 50 may be formed with a partition 55 which separates the input of the respiratory gas to the patient from the sensing of the gas temperature for controlling the operation of the heater 15. The positioning of the sensor 60 in this manner, in the nose cannula 50 in thermal contact with the respiratory gas at the point of administration of the gas to the patient, 56, results in substantially reducing or eliminating the effect that ambient room temperature and humidity might have on control of the gas temperature and moisture content. It is to be understood, however, that the nose cannula 50 may be constructed without the partition 55 separating the input of the respiratory gas to the patient from the sensing of the gas temperature. In such an embodiment the sensor 60, however, is still to be positioned in substantially direct thermal contact with the respiratory gas at the point of administration, 56, of the gas to the patient.

As best shown in the embodiment of FIG. 6, the nose cannula 50 is constructed without the partition 55, and the sensor 60 is still positioned directly adjacent to the point of administration, 56, of the gas to the patient.

The foregoing description of a preferred embodiment for this invention has been presented for purposes of illustration and description. It is not intended to be exhaustive or to limit the invention to the precise form disclosed. Obvious modifications or variations are possible in light of the above teachings. The embodiment described has been chosen and described in an effort to provide the best illustrations of the principles of the invention and its practical application, and to thereby enable one of ordinary skill in the art to utilize the invention in various embodiments and with various modifications as are suited for the particular use contemplated. All such modifications and variations are within the scope of the invention as determined by the appended claims when interpreted in accordance with the breadth to which they are fairly, legally, and equitably entitled.

Also, this application was prepared without reference to any particular dictionary. Accordingly, the definition of the terms used herein conforms to the meaning intended by the inventors acting as their own lexicographer in accordance with the teaching of the application, rather than any dictionary meaning which is contrary to or different from the inventors' meaning regardless of the authoritativeness of such dictionary.

Referring now to the embodiment of FIG. 7, the nose cannula 50 is constructed with a partition 55a that directs the flow of the respiratory gas in a first flow path of movement directly into contact with the sensor 60 through which the temperature of the respiratory gas is controlled. The respiratory gas thereafter passes in a second flow path essentially directly to the cannula outlets 56 for application to the patient. In this manner the effect that ambient room temperature and humidity might have on control on the respiratory gas temperature and moisture control is diminished while obtaining the benefits of the sensor 60 being positioned in substantially direct thermal contact with the respiratory gas at the point of administration 56 of the gas to the patient.

What is claimed is:

1. Apparatus for controlling the delivery of a respiratory gas to a user comprising:

heating means including a heating element for heating a respiratory gas to a temperature sufficient to be delivered in a flow path to a user at a predetermined temperature level;

respiratory gas conveying means for moving said respiratory gas in a first flow path and subsequently in a second flow path at a predetermined rate to a user;

said respiratory gas conveying means including a delivery tube having a first portion containing said heating element, with said first portion being connected at a distal end to means for administering respiratory gas to a user;

said heating element having a distal end portion positioned adjacent the distal end of said first delivery tube portion;

said delivery tube including a second portion having a distal end connected to means for administering respiratory gas to a user, with said distal end of said second portion occluded from the flow of respiratory gas through said second portion;

means for administering said respiratory gas to said user at said predetermined flow rate and at said predetermined temperature level; and monitoring means in thermal contact with said respiratory gas moving in said first flow path for monitoring the temperature of said respiratory gas prior to the administration of said respiratory gas in said second flow path essentially directly to said user, said monitoring means including a sensor fixedly secured to the distal end of said second portion occluding the flow of respiratory gas through said second portion and positioned transversely across said first flow path in thermal contact with said respiratory gas and forming a wall for directing the flow of respiratory gas in said second flow path.

2. The apparatus for controlling the delivery of a respiratory gas to a user as defined in claim 1 further including humidifying means for humidifying said respiratory gas to a predetermined level prior to administering said respiratory gas to said user.

3. The apparatus for controlling the delivery of a respiratory gas to a user as defined in claim 1 wherein said means for administering said respiratory gas to said user at said predetermined flow rate and at said predetermined temperature level includes a nose cannula.

4. The apparatus for controlling the delivery of a respiratory gas to a user as defined in claim 3 wherein said monitoring means for monitoring the temperature of said respiratory gas is a sensor carried by said nose cannula.

5. The apparatus for controlling the delivery of a respiratory gas to a user as defined in claim 4 wherein said monitoring means includes a temperature sensor positioned in direct contact with said respiratory gas moving in said first respiratory gas flow path.

6. Apparatus for controlling the delivery of a respiratory gas to a user comprising:

a respiratory gas heater including a heating element for heating a respiratory gas to a predetermined temperature sufficient to be delivered in a first flow path and a subsequent second flow path at a predetermined flow rate to a user at a predetermined temperature level;

a delivery tube having a first portion containing said heating element, with said first portion being connected at a distal end to a nose cannula for administering respiratory gas to a user;

said heating element having a distal end portion positioned adjacent the distal end of said first delivery tube portion;

said delivery tube including a second portion having a distal end connected to the nose cannula for administering respiratory gas to a user, with said distal end of said second portion occluded from the flow of respiratory gas through said second portion;

a nose cannula for administering said respiratory gas to said user at said predetermined flow rate and at said predetermined temperature level; and a temperature sensor in thermal contact with said respiratory gas moving in said first flow path for monitoring the temperature of said respiratory gas prior to the administration of said respiratory gas in said second flow path essentially directly to said user, said temperature sensor fixedly secured to the distal end of said second portion of said delivery tube occluding the flow of respiratory gas through said second portion and positioned transversely across said first flow path in thermal contact with said respiratory gas and forming a wall for directing the flow of respiratory gas in said second flow path.

7. The apparatus for controlling the delivery of a respiratory gas to a user as defined in claim 6 wherein said temperature sensor is positioned in said nose cannula adjacent to said point at which said respiratory gas is discharged from said nose cannula.

* * * * *